US012788942B2

(12) United States Patent
Duering et al.

(10) Patent No.: US 12,788,942 B2
(45) Date of Patent: Nov. 10, 2026

(54) MAGNETIC RESONANCE IMAGING SAFE (MR-SAFE) CONTROL CORD

(71) Applicant: MaRVis Interventional GmbH, Garmisch-Partenkirchen (DE)

(72) Inventors: Klaus Duering, Wallgau (DE); Nasib Dlaikan-Campos, Wuerselen (DE); Areli Graciela Luttmann, Verden (DE)

(73) Assignee: MaRVis Interventional GmbH, Garmisch-Partenkirchen (DE)

( * ) Notice: Subject to any disclaimer, the term of this patent is extended or adjusted under 35 U.S.C. 154(b) by 253 days.

(21) Appl. No.: 18/497,481

(22) Filed: Oct. 30, 2023

(65) Prior Publication Data

US 2024/0091496 A1 Mar. 21, 2024

Related U.S. Application Data

(63) Continuation-in-part of application No. PCT/EP2022/061592, filed on Apr. 29, 2022.

(30) Foreign Application Priority Data

Apr. 29, 2021 (DE) .................... 10 2021 111 091.2

(51) Int. Cl.
*A61M 15/00* (2006.01)
*A61B 90/00* (2016.01)
(Continued)

(52) U.S. Cl.
CPC ......... *A61M 25/0053* (2013.01); *A61B 90/39* (2016.02); *A61M 25/0147* (2013.01); *G01R 33/288* (2013.01); *A61B 2090/3954* (2016.02)

(58) Field of Classification Search
CPC .... A61B 2090/3954; A61B 2090/3966; A61B 90/39; A61M 2205/32; A61M 25/0009;
(Continued)

(56) References Cited

U.S. PATENT DOCUMENTS

| | | | |
|---|---|---|---|
| 5,556,496 | A | 9/1996 | Sumerak |
| 10,035,002 | B2 | 7/2018 | Weiss |

(Continued)

FOREIGN PATENT DOCUMENTS

| | | | |
|---|---|---|---|
| DE | 696 05 645 | T2 | 6/2000 |
| DE | 102011081445 | A1 | 2/2013 |

(Continued)

OTHER PUBLICATIONS

EPO Examination Report, mailed on Dec. 8, 2025, from European Application No. 22727046.9, filed on Apr. 29, 2022. 22 pages.

(Continued)

*Primary Examiner* — Mark D Remaly
(74) *Attorney, Agent, or Firm* — HoustonHogle LLP

(57) ABSTRACT

A magnetic resonance imaging (MR) safe control cord is provided for controlling a medical device. The control cord can be arranged in a medical device, wherein the control cord is formed from a non-ferromagnetic matrix material in which a reinforcing material is embedded, and wherein the control cord is structurally designed in such a way that the medical device can be controlled by displacing the control cord in and against an axial direction of a medical device, or that a functional element of a medical device which can be coupled to the control cord can be controlled.

13 Claims, 1 Drawing Sheet

(51) Int. Cl.

| | |
|---|---|
| ***A61M 25/00*** | (2006.01) |
| ***A61M 25/01*** | (2006.01) |
| ***G01R 33/28*** | (2006.01) |

(58) Field of Classification Search

CPC .......... A61M 25/0053; A61M 25/0147; B29C 70/52; B29C 70/526; G01R 33/288

See application file for complete search history.

(56) References Cited

U.S. PATENT DOCUMENTS

| | | | |
|---|---|---|---|
| 2010/0198049 | A1 | 8/2010 | Karmarkar et al. |
| 2015/0290423 | A1 | 10/2015 | Storbeck et al. |
| 2020/0307127 | A1 | 10/2020 | Morishima et al. |

FOREIGN PATENT DOCUMENTS

| | | | |
|---|---|---|---|
| DE | 102014116566 | A1 | 5/2016 |
| GB | 2259044 | A | 3/1993 |
| KR | 20080022997 | A | 3/2008 |
| WO | WO 2009141165 | A2 | 11/2009 |
| WO | WO 2014086917 | A1 | 6/2014 |
| WO | WO 2015161927 | A1 | 10/2015 |
| WO | WO 2017037130 | A1 | 3/2017 |
| WO | WO 2017216809 | A2 | 12/2017 |
| WO | WO 2018206068 | A1 | 11/2018 |

OTHER PUBLICATIONS

International Search Report and Written Opinion of the International Searching Authority, mailed on Jan. 16, 2023, from International Application No. PCT/EP2022/061592, filed on Apr. 29, 2022. 31 pages.

German (DE) Search Report, mailed on Feb. 19, 2022, from German Application No. 10 2021 111 091.2. 6 pages.

International Preliminary Report on Patentability, mailed on Nov. 9, 2023, from International Application No. PCT/EP2022/061592, filed on Apr. 29, 2022. 14 pages.

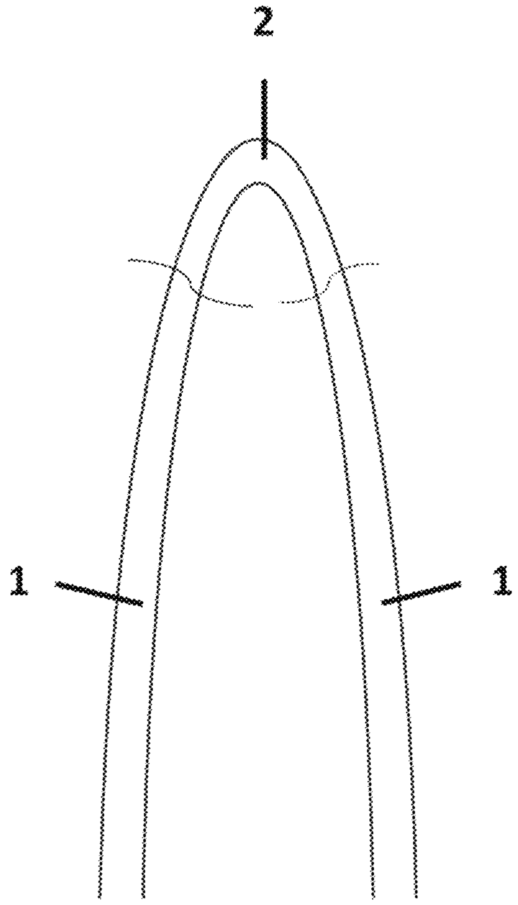
2
1
1

MAGNETIC RESONANCE IMAGING SAFE (MR-SAFE) CONTROL CORD

RELATED APPLICATIONS

This application is a Continuation-in-Part of International Application No. PCT/EP2022/061592, filed on Apr. 29, 2022, now International Publication No. WO 2022/229443 A2, published on Nov. 3, 2022, which International Application claims priority to German Application No. 10 2021 111 091.2, filed on Apr. 29, 2021, both of which are incorporated herein by reference in their entirety.

BACKGROUND OF THE INVENTION

Control cords are used in medical devices, for example, to control the device and/or to pull and/or push parts of the device. In conventional medical devices of this type, these control cords are made of metal. These medical devices can be used in X-ray guided medical procedures, but not in magnetic resonance imaging (MRI) guided medical procedures, because metals in MRI are electrically conductive and can heat up, which can endanger the patient and the doctor.

Examples of such medical devices include steerable catheters, steerable sheaths, stent delivery systems, delivery systems for occluders, coil delivery systems, atrial flow regulator delivery systems, bioptomes, TAVR, TMVR & LAA delivery systems, steerable ablation catheters, thrombectomy systems, steerable needles, steerable guidewires, etc.

WO 2015/161927 describes a medical instrument insertable into a human or animal body, the medical instrument comprising an instrument body, the instrument body comprising at least one poorly electrically conductive rod-shaped body formed of a matrix material and non-metallic filaments.

U.S. Pat. No. 10,035,002 B2 shows a guide wire. This has a sensor with a cable and is not MR safe.

Conventional pultrusion devices are described in DE 696 05 645 T2 and U.S. 2020/0 307 127 A1.

U.S. 2010/0198049 A1 discloses catheter with a steerable tip that has already been invented for use in MRI, but can only be used in MRI under certain conditions because it is not MR safe, but only MR conditional. The control cords are designed as conductive metal wires to make the catheter visible at the tip by an active MR marker. This entails the risk of danger to patients and physicians if the permitted limited conditions of use of such a product in interventional MRI are not fully adhered to.

SUMMARY OF THE INVENTION

The present invention relates to a magnetic resonance imaging (MR) safe control cord.

The object of the present invention is to provide an alternative to prior art control cords for medical devices.

Another task is to provide control cords with improved mechanical properties.

Furthermore, it is an object of the present invention to provide control cords, in particular for medical devices, as well as such a medical device, which can be manufactured in a simple manner and/or with high quality.

A further task is to provide a method for manufacturing such control cords.

To solve these tasks, the invention has the features indicated in the independent patent claims. Advantageous embodiments thereof are indicated in the respective subclaims.

According to the invention, a magnetic resonance imaging (MR) safe control cord is provided for controlling a medical device. The control cord can be arranged in a medical device, wherein the control cord is formed from a non-ferromagnetic matrix material in which a reinforcing material is embedded, and wherein the control cord is structurally designed in such a way that the medical device can be controlled by displacing the control cord in and against an axial direction of a medical device, or that a functional element of a medical device which can be coupled to the control cord can be controlled.

A control of a functional element of a medical device can, for example, be understood to be a displacement, preferably in and against an axial direction of the medical device, and/or a rotation and/or an opening and/or a closing of the functional element (e.g. forceps of a bioptome).

In steerable tubular medical devices, such as catheters, metal wires are often used as traction or control cords. However, due to the electrical conductivity of metal wires and the associated heating, such metal wires cannot be used in magnetic resonance imaging (MRI) procedures.

By forming the control cord according to the invention from a non-ferromagnetic matrix material in which a reinforcing material (one or more non-metallic reinforcing fibers) is embedded, an MR-safe control cord is provided. Such a control cord is an alternative to known control cords formed from a single material.

In the context of the present invention, the term "magnetic resonance imaging-safe" means an MR-safe article as defined in ASTM standard F2503-13.

According to ASTM standard F2503-13, this means: "MR-safe—an article that poses no known hazards when exposed to an MR environment. MR-safe items are made of materials that are electrically non-conductive, non-metallic and non-magnetic.

Non-metallic means that the control cord must not contain any metal parts with a length greater than 1 cm. However, the control cord may contain small dispersed amounts of metal microparticles as MR marker particles. The amount of metal microparticles may be a maximum of 10 wt % (w/w) or 10 wt % or 5 wt % or 4 wt % or 3 wt % or 2 wt % or 1 wt % or 0.5 wt %. In the context of the present invention and also according to the ASTM standard, such marker concentrations are referred to as non-metallic materials.

Accordingly, a control cord according to the invention is electrically non-conductive and non-magnetic and non-metallic. This means that the control cord consists of electrically non-conductive and non-metallic and non-magnetic materials.

A fiber composite material may be provided as the starting material for an MR-safe control cord according to the invention. This comprises the reinforcement material, which may in particular be formed from fibers embedded in the matrix material.

Both thermoset and thermoplastic polymers can be used as matrix materials. The relatively inexpensive polyester resins, vinyl ester resins and epoxy resins are used as duroplastic matrix materials. In order to improve special properties such as sliding properties, subsequent deformability under heat or abrasion resistance, thermoplastic fiber composites can also be produced. Polyamides, polypropylenes and polyethylenes are used as matrix materials.

The matrix material can thus be a plastic, such as epoxy resin, polyester resin, vinyl ester resin, polyamide, PEEK, PEBAX, polyethylene, polypropylene, polyurethane, silicone, polylactic acid polymers.

In the context of the present invention, a reinforcing material is understood to mean one or more reinforcing fibers. Reinforcing fibers include fibers, filaments, fiber bundles, filament bundles.

Furthermore, in the context of the present invention, a reinforcing material is understood to mean reinforcing fiber composites. Reinforcing fiber composites include scrims, woven fabrics and non-woven fabrics. These are defined as follows:

A fiber or filament is a linear, elemental structure formed from a fibrous or filamentary material. The fiber or filament can be endless or limited in length and is a thin structure in relation to its length. To speak of a fiber or filament in the technical field, the ratio of length to diameter should be at least between 3:1 and 10:1.

Fiber bundles or filament bundles comprise fibers or filaments that extend substantially all in one longitudinal direction or axial direction, preferably over approximately an entire length of a control cord.

The fiber bundles or filament bundles can also extend over approximately 75% to 100% of the total length of the control cord.

Ravings comprise at least two and preferably several fiber or filament bundles without twist, which are arranged approximately parallel to each other.

Yarns comprise at least two and preferably more fiber or filament bundles with twist, i.e. that the fiber bundles are arranged in a twisted manner.

A fiber or filament composite formed as a scrim is a loose composite of fibers or filaments that extend in space, preferably in the longitudinal and transverse directions and, if necessary, also in a third direction perpendicular to the longitudinal and transverse directions.

A fiber or filament composite formed as a fabric is a solid composite of fibers or filaments that extend in space, preferably in the longitudinal and transverse directions and, if necessary, also in a third direction perpendicular to the longitudinal and transverse directions.

A nonwoven fabric is a structure of fibers or filaments of limited length, continuous fibers or filaments, or chopped yarns of any kind and origin, which have been assembled in some way into a nonwoven (a fiber or filament layer, a fiber or filament pile) and bonded together in some way. Nonwoven fabrics are for the most part flexible sheet materials, i.e. they are easily bendable, their main structural elements are fibers or filaments and they have a comparatively small thickness compared to their length and width.

The reinforcement material can be made of natural or synthetic materials, e.g. glass, aramid or Kevlar®, ceramic, UHMWPE (ultra-high molecular weight polyethylene), polyamide, polypropylene, PEEK, polyethylene terephthalate (PET), rayon (e.g. HL fibers), Dacron, vegetable fibers (e.g. silk, sisal, hemp, cotton, etc.), or spider silk fibers or mixtures thereof.

Preferably, aramid or Kevlar®, UHMWPE (Ultra High Molecular Weight Polyethylene), polyamide, polypropylene and spider silk fibers or combinations thereof are provided as reinforcing fibers.

This allows the properties to be varied in absolute terms as well as in their relationship between longitudinal and transverse direction over a wide range.

Since metal wires cannot be used in magnetic resonance imaging (MRI) procedures due to the electrical conductivity of metal wires and an associated heating, traction cords made of pure aramid fiber bundles (Kevlar®) without matrix material and PEEK strands without matrix material are also used.

Kevlar® fibers or fiber bundles or PEEK strands are thus already known as control cords for MR-compatible medical devices, but they have an increased elongation compared to metal wires and thus do not have a comparably low elongation under tensile load as metal wires. These mechanical disadvantages lead to problems in handling and reproducibility of handling such medical devices.

The MR-safe control cord according to the invention provides an alternative to metal wires, Kevlar® fibers or fiber bundles or PEEK strands.

The MR-safe control cord according to the invention has improved mechanical properties, in particular lower elongation, than, for example, Kevlar® fibers (without matrix material) and PEEK strands, due to the design shown above.

A particularly important factor is that the control cords have the lowest possible elongation, as control cords are mostly loaded in tension during operation. In contrast, the elongation of rod-shaped bodies plays a subordinate role. The only decisive factor here is that they do not tear and can be completely removed from the human body.

A control cord may have a diameter of 1 mm, or less than 0.9 mm, or less than 0.8 mm, or less than 0.7 mm, or less than 0.6 mm, or less than 0.5 mm, or less than 0.4 mm, or less than 0.3 mm, or less than 0.2 mm, or less than 0.1 mm, or less than 0.05 mm.

A control cord may have a diameter of 1 mm or greater 0.9 mm or greater 0.8 mm or greater 0.7 mm or greater 0.6 mm or greater 0.5 mm or greater 0.4 mm or greater 0.3 mm or greater 0.2 mm or greater 0.1 mm or greater 0.05 mm.

A control cord can thus have a diameter of at least 0.02 mm or 0.05 mm or 0.1 mm or 0.2 mm or 0.3 mm or 0.4 mm or 0.5 mm and a maximum diameter of 0.6 mm or 0.7 mm or 0.8 mm or 0.9 mm or 1.0 mm or 1.1 mm (diameter from 0.02 mm to 1 mm).

The control cord can preferably be produced by pultrusion and/or extrusion.

In the context of the present invention, pultrusion is understood to be a process in which chemically reactive polymers/resins are crosslinked as the matrix material of the pultrudate.

Chemical reaction processes for pultrusion can be, in particular, radical or ionic cross-linking of polymers, such as unsaturated polyesters, etherification and esterification of polysaccharides, hydrolysis of polyvinyl esters, or acetalization of polyvinyl alcohol.

The matrix material may be doped with magnetic resonance imaging artifact-generating marker particles such that the medical device is visible in magnetic resonance imaging through these marker particles, wherein the magnetic resonance imaging artifact-generating marker particles are preferably arranged along substantially the entire length of the control cord such that the medical device becomes visible along substantially its entire length in magnetic resonance imaging.

The marker particles are embedded in the matrix material.

Such marker particles may be formed of metal, but their proportion in the control cord is too low, so that the control cord is still classified as MR-safe. The marker particles are passive-negative MR markers, preferably selected from the following metals or metal compounds: Iron (Fe), Cobalt (Co), Nickel (Ni), Molybdenum (Mo), Zirconium (Zr), Titanium (Ti), Manganese (Mn), Rubidium (Rb), Aluminium (Al), Palladium (Pd), Platinum (Pt), Chromium (Cr) or Chromium Dioxide ($CrO_2$) or Iron Oxide (FeO, Fe2O3, Fe3O4).

MR-safe control cords according to the invention can thus be visualized by the incorporation of small amounts of passive-negative MR marker particles in MRI, preferably by sharp limited artifacts.

Additionally or alternatively, the control cord may also have X-ray markers. Visualization of the control cord during X-ray examinations can be realized by embedded X-ray marker particles at a distal end of the control cord.

By providing an MR marker and/or an X-ray marker, the control cord or a medical device comprising at least one control cord is visible in magnetic resonance imaging and/or in X-ray examinations.

By combining MR markers and X-ray markers, the control cords according to the invention can be visualized in both imaging techniques simultaneously.

The introduction of MR markers and/or X-ray markers into a medical device can be easily realized by using an appropriately doped control cord. Such control cords can be produced cheaply in different dopings as a mass product and with an exact dosage of the marker particles. In the manufacture of a medical device, the use of one or more corresponding control cords with MR markers and/or X-ray markers can thus ensure the visualization of the medical device in a magnetic resonance tomography and/or an X-ray examination.

The control cord may further comprise a central section and a peripheral section extending in an axial direction of the control cord, wherein the central section is centrally located with respect to a cross-section of the control cord and is radially surrounded by the peripheral section, and wherein both the central section and the peripheral section extend substantially along the entire length of the control cord, and the central section comprises at least one reinforcing fiber embedded in a non-ferromagnetic matrix material, the matrix material being doped with MR marker particles, and the peripheral section comprises an undoped, non-ferromagnetic matrix material.

The diameter of the central section is preferably less than or equal to 0.2 mm, preferably less than or equal to 0.15 mm and even more preferably less than or equal to 0.1 mm and even more preferably less than or equal to 0.08 mm and in particular less than or equal to 0.05 mm. By doping only the matrix material of the very small central section with MR marker particles, a particularly narrow and sharp artifact is generated during magnetic resonance imaging.

Such a concentrated arrangement of a smaller amount of MR marker particles is advantageous over that with a higher amount of MR marker particles distributed over the entire cross-section of the control cord, as the voxels are blackened along the concentrated arrangement of MR particles, but these voxels have the same degree of blackening as with a larger amount of MR marker particles distributed over a correspondingly larger area. As a result, fewer voxels are blackened in width and a narrower image of the medical instrument is achieved, so that less target tissue can be covered by blackening in the MRI image.

Therefore, with a control cord according to the invention with passive-negative MR marker doping only in its central section, it is possible to generate a representation in magnetic resonance imaging that is approximately as narrow as for a metallic control cord in an X-ray imaging process.

This applies in particular if the control cord has only one doped reinforcing fiber, or in the case of several reinforcing fibers, whereas only the matrix material of the centrally arranged reinforcing fiber has MR markers. Preferably, the reinforcement fiber provided with marker particles in the matrix material is then arranged in the center of the control cord. This maximizes the distance between the doped central section of the control cord and the surface of the medical device. This results in water or fat molecules in the examined body not being able to get closer to the central section than the surface of the medical device. This keeps the resonance between the MR markers and the water or fat molecules low, which means that the artifacts generated by the MR markers are small and the medical device appears as a narrow line in an MR imaging process.

In addition, it has been shown that due to the concentration of MR markers on the central section, the proportion of MR markers in the matrix material can vary over a wide range without significantly affecting the representation of the medical device in the MR imaging process. When iron particles with a particle size of 0 to 20 μm were used, essentially the same representation was obtained with a weight ratio of about 1:5 to about 1:30 between markers and matrix material. It has been shown that the local concentration on an area that is as small as possible per se, i.e. the central section, has considerably more influence on the representation in the MR imaging procedure than the proportions of marker particles in the matrix material.

The invention for the first time such thin control cords with a structure that can have a central section and a peripheral section are created.

A control cord is a one-piece solid body. It is not a tubular or hose-shaped hollow body.

In particular, the matrix material of the control cord is formed as a homogeneous matrix material. The matrix material of the peripheral section and the central section thus preferably consist of the same type of material.

Preferably, the reinforcing material in the peripheral section is arranged approximately evenly with respect to the cross-section. In this way, a high torsional and bending strength is achieved even with a thin or small-volume peripheral section.

It has also been shown that by concentrating in the central section, the total amount of MR marker is very small and yet a very good image is obtained. In this way, the best possible imaging of a medical device comprising such a control cord with doping only in the central section is achieved.

A reinforcing fiber may comprise at least one elongate fiber or a plurality of elongate fibers and preferably a plurality of elongate fibers arranged in parallel or interlaced or twisted together. By comprising at least one elongated fiber or a plurality of elongated fibers, the reinforcing fiber provides the control cord with high strength in the longitudinal direction. Such an orderly formation and arrangement of the reinforcing fiber in the control cord results in better product quality.

The reinforcing fiber in the central section may be an ht fiber bundle and the reinforcing fiber in the peripheral section may be a glass fiber bundle.

An ht-fiber bundle is a high-strength fiber bundle. Typical examples of ht fiber bundles are aramid fibers and UHMWPE fibers (Ultra High Molecular Weight Polyethylene Fibers). ht fiber bundles have a tensile or tear strength of at least 20 cN/tex. Optionally, the ht fiber bundles have a tensile or tear strength of at least 32 cN/tex and in particular of at least 30 cN/tex.

An ht-fiber bundle is highly flexible or bendable and has a high tensile or tear strength. In addition, the ht fiber bundle embedded in the matrix material gives the control cord a certain stiffness.

Glass fiber bundles are stiffer than ht fiber bundles, so that a control cord that has both ht fiber bundles and glass fiber bundles is preferred. A control cord that has both ht-fiber bundles and glass-fiber bundles can be optimally adjusted in terms of its stiffness and flexibility, and in particular in terms of its torsional stiffness.

The arrangement of at least one glass fiber bundle in the peripheral section enables the highest possible stiffness. The at least one peripheral glass fiber bundle gives the control cord the necessary compression and bending stiffness for shear load. Due to the fact that at least one ht-fiber bundle is arranged centrally on a neutral line, the at least one ht-fiber bundle only minimally reduces the compression and bending stiffness of the control cord. In technical mechanics, the neutral line, also called the zero line, is the layer of a cross-section of a control cord whose length does not change during a bending process. There, the bending does not cause any tensile or compressive stresses. The surface runs through the geometric center of gravity of the cross-sectional area of the control cord.

The at least one reinforcing fiber in the central section can also be a glass fiber bundle and the at least one reinforcing fiber in the peripheral section can be an ht fiber bundle. This arrangement is optimal if the control cord is to have a low proportion of glass fibers and a high proportion of ht fibers. In this embodiment, a control cord consisting predominantly of the more flexible ht fiber is reinforced in compression and bending stiffness by the glass fibers.

It is advantageous to arrange the reinforcing fibers contained in the larger proportion on the surface of the control cord and the reinforcing fibers contained in the smaller proportion on the inside in order to obtain a homogeneous surface. The product quality is thereby significantly increased. The proportion of reinforcing fibers in the interior is at least greater than 5 vol. % or 10 vol. % or 15 vol. % or 20 vol. % or 25 vol. % or 30 vol. % or 35 vol. % or greater than 40 vol. %.

The reinforcing fibers are electrically non-conductive fibers or filaments so that they can be used during magnetic resonance imaging. Accordingly, the term reinforcing fiber as used in the present description excludes any electrically conductive fibers, such as thin metal wires or a carbon filament.

Preferably, a reinforcing fiber is formed from several fibers. Such a fiber bundle is referred to as "roving".

When the fibers of the reinforcing fiber are twisted together, they form a yarn. Such a bundle of fibers is called a "yarn".

All reinforcing fibers in the control cord can be ht-fiber bundles. A control cord designed in this way has the best possible properties in terms of tensile strength.

Furthermore, all reinforcing fibers in the control cord can be glass fiber bundles. Such a control cord has the best possible properties in terms of compression and bending stiffness.

The non-ferromagnetic matrix material in the central section and in the peripheral section may be the same non-ferromagnetic matrix material. The matrix material is preferably epoxy resin.

The marker particles in the central section are preferably MR marker particles.

One or more reinforcing fibers may be provided in the central portion and at least three or four or five or six or seven or eight or nine or ten or eleven or twelve reinforcing fibers may be provided in the peripheral portion radially circumferentially around the reinforcing fiber of the central portion and spaced approximately equally apart.

MR-safe control cords according to the invention are electrically non-conductive and do not heat up. Due to their design and material, they have good mechanical properties similar to those of metal wires. Due to the centric doping, the MR-safe control cords or medical devices containing such control cords can be imaged well in MRI with a sharp artifact.

A control cord made of a metal wire has very good mechanical properties. A control cord made of Kevlar® fibers or PEEK filaments, on the other hand, has poor mechanical properties in terms of tensile strength, yield strength and modulus of elasticity, especially with regard to elongation.

A control cord according to the invention made of a fiber composite material can be structurally designed in such a way that

- a tensile strength is greater than that of a control cord formed from Kevlar® fibers or PEEK filaments, and/or that
- a yield strength is smaller than that of a control cord formed of Kevlar® fibers or PEEK filaments, and/or that
- a modulus of elasticity smaller than that of a control cord formed from Kevlar® fibers or PEEK filaments.

Furthermore, since the control cords according to the invention are made of non-metallic materials, they are electrically non-conductive and do not heat up and are therefore MR-safe.

The mechanical properties (tensile strength, yield strength and modulus of elasticity) of a control cord according to the invention lie between those of a control cord made of metal wires and those of a control cord made of Kevlar® fibers or PEEK filaments. For individual parameters, depending on the composite material, it may also be possible to achieve better properties than with a metal wire.

In order to achieve a lower elongation and a high strength in the longitudinal direction, the elongation at break and the breaking strength of the control cord according to the invention are of utmost importance.

This means that a control cord according to the invention can have a maximum elongation at break of 4% or 3.5% or 3% or 2.5% or 2% or 1.5% or 1% (4% to 1%) due to the material composition used.

This means that a control cord according to the invention can have a tensile strength (ultimate tensile strength) of at least 3.5 GPa or 4 GPa or 4.5 GPa to 5 GPa or 5.5 GPa and a maximum of 6 GPa (3.5 to 6.0 GPa) due to the material composition used.

This means that a control cord according to the invention can have a minimum tensile modulus (tensile strength; tensile modulus) of at least 75 GPa or 100 GPa or 125 GPa or 150 GPa or 175 GPa or 200 GPa (75 GPa to 200 GPa) due to the material composition used.

This means that a control cord according to the invention can have a minimum compression strength of 200 MPa or 250 MPa or 300 MPa or 400 MPa or 500 MPa to 600 MPa or 750 MPa or 1,000 MPa due to the material composition used.

A maximum compressive strength can be 1,500 MPa or 2,000 MPa or 2,500 MPa (200 MPa to 1000 MPa).

This means that a control cord according to the invention can have a minimum modulus of elasticity of at least 75 GPa or 85 GPa or 90 GPa or 100 GPa due to the material composition used. A maximum modulus of elasticity can be at most 115 GPa or 130 GPa or 140 GPa or 150 MPa (75 GPa to 150 MPa).

Advantages of the fiber composites according to the invention for the production of MR-safe control cords compared to control cords made of e.g. Kevlar® fibers or PEEK filaments are, among others, a lower elongation under tensile load and/or a higher stiffness under shear sload and/or a higher tensile strength and thus a better, stable and reproducible functionality as a control cord, which is closer to the functionality of a control cord made of metal wires.

The control cord may be structurally configured to be disposable in one or more lumens in a sheath wall and/or in a central lumen of a tubular medical device or in a lumen in a medical device comprising a solid body.

In order to improve an arrangement of the control cord in a lumen of a medical device, the control cord can have at least one fastening section and/or a deflection section, wherein nodes or drivers (crimped on) are provided in the region of the fastening section, or the matrix material is designed to be weldable at least in this region, and wherein the matrix material is designed to be more flexible in the region of the deflection section than in the rest of the control cord.

For these embodiments of a control cord according to the invention, matrix materials with a lower stiffness and/or a higher flexibility than in the remaining area of the control cord are provided for the attachment section and/or the deflection section.

A higher material load acts on the control cord at deflection sections if the control cord is arranged continuously from the proximal end via a deflection point at the distal end and running back to the proximal end.

In the area of the deflection section, the control cord can then have a higher sliding ability and/or flexibility than over the rest of its length.

Furthermore, a thin tube or shrink tube made of a material with high sliding properties, e.g. PTFE or FEP, can be applied or arranged on a surface of the control cord. A PTFE or FEP shrink hose can have a wall thickness of approximately 0.03 mm, 0.04 mm, 0.05 mm, 0.06 mm, 0.07 mm, 0.8 mm, 0.09 mm, 0.1 mm.

By providing such a hose or hose piece or section, an increased sliding ability of the control cord is achieved, as the friction (or coefficient of friction) is reduced compared to that of the fiber composite material.

By providing a hose or a suitable coating of the control cord in the area of the deflection point(s), the friction in the bend is reduced and the fiber composite is stabilised.

Sliding materials can also be applied by extrusion, coating, dip coating, vapour deposition and similar processes. Alternatively, this surface material could also be applied in-line by pultrusion, possibly by a second step in the manufacturing process.

When using a control cord according to the invention in a medical device, it may be envisaged that a control cord has to be deflected in order to fulfil a certain technical function. Such a section of the control cord, which is arranged in a medical device in the area of a deflection point for the control cord, in which the control cord is deflected, is referred to below as a deflection section.

In such a deflection point, higher mechanical load can occur in a corresponding deflection section of a control cord due to bending, displacement and/or friction.

A control cord may have one or more deflection sections spaced apart in a longitudinal direction.

In a deflection section, the matrix material of the control cord has a lower stiffness and/or a higher flexibility than the matrix material of the remaining area of the control cord (main section).

A preferred embodiment of a control cord made of fiber composite material according to the invention has a lower stiffness and/or a higher flexibility in the deflection section. The deflection section comprises a section of the fiber composite material in the region of the deflection point of the medical device, in which the matrix material of the control cord has a lower stiffness and/or a higher flexibility than the matrix material of the main section.

A matrix material with a lower stiffness and/or a higher flexibility can be obtained by using a thermoset with a lower Shore hardness, e.g. less than 46D or 39D or 29D or 25D, or by a lower cross-linking of a reactive polymer/resin. It is most preferred to form a gradient of the two matrix materials, so that no predetermined breaking point occurs at the position of the matrix material change.

This can be achieved, for example, by changing the matrix material from epoxy resin to polyurethane.

The above and other features of the invention including various novel details of construction and combinations of parts, and other advantages, will now be more particularly described with reference to the accompanying drawings and pointed out in the claims. It will be understood that the particular method and device embodying the invention are shown by way of illustration and not as a limitation of the invention. The principles and features of this invention may be employed in various and numerous embodiments without departing from the scope of the invention.

BRIEF DESCRIPTION OF THE DRAWINGS

The present invention is described in more detail below on the basis of an example of an embodiment shown in the FIGURE:

FIG. 1 a schematic view of an exemplary embodiment of a control cord according to the present invention.

DETAILED DESCRIPTION OF THE PREFERRED EMBODIMENTS

According to the present invention magnetic resonance imaging (MR) safe control cord 1 for controlling a medical device is provided as shown in FIG. 1, wherein the control cord 1 can be arranged in a medical device (not shown), wherein the control 1 cord is formed from a non-ferromagnetic matrix material in which a reinforcing material is embedded, and wherein the control cord 1 is structurally designed in such a way that the medical device can be controlled by displacing the control cord 1 in and against an axial direction of a medical device, or that a functional element (not shown) of a medical device which can be coupled to the control cord can be controlled.

The control cord 1 has at least one deflection section 2, the deflection section 2 being formed with matrix materials having a lower stiffness and/or a higher flexibility than in the remaining region of the control cord.

The matrix material is doped with magnetic resonance imaging artifact-generating marker particles such that the medical device is visible in magnetic resonance imaging by these marker particles, whereas the magnetic resonance imaging artifact-generating marker particles are preferably arranged over substantially the entire length of the control cord 1 such that the medical device is visible in magnetic resonance imaging over substantially its entire length and/or that the control cord comprises one or more X-ray markers.

The control cord 1 is structurally designed in such a way that it can be arranged in one or more lumens in a sheath wall (not shown) and/or in a central lumen (not shown) of a tubular medical device, and has a diameter of 0.02 mm to 1 mm, i.e. of 1 mm, or smaller than 0.9 mm, or smaller than 0.8 mm, or smaller than 0.7 mm, or smaller than 0.6 mm, or smaller than 0.5 mm, or smaller than 0.4 mm, or smaller than 0.3 mm, or smaller than 0.2 mm, or smaller than 0.1 mm, or smaller than 0.05 mm.

A structural design is achieved in that the matrix material is a duroplastic or a thermoplastic polymer, and/or that the reinforcing material comprises one or more reinforcing fibers which are formed as fibers, filaments, fiber bundles, filament bundles which preferably extend over approximately the entire length of the control cord, and/or in that the control cord has an elongation at break of 4% to 1%, which is a maximum of 4% or 3.5% or 3% or 2.5% or 2% or 1.5% or 1%, and/or that the control cord has an ultimate tensile strength of 3.5 to 6.0 GPa, which is at least 3.5 GPa or 4 GPa or 4.5 GPa or 5 GPa or 5.5 GPa and at most 6 GPa.

The control cord 1 comprises a central section (not shown) and a peripheral section (not shown) extending in the axial direction of the control cord 1, the central section being centrally located with respect to a cross-section of the control cord and being radially surrounded by the peripheral section, and whereas both the central section and the peripheral section extend substantially over the entire length of the control cord, and the central section comprises at least one non-metallic reinforcing material embedded in a non-ferromagnetic matrix material, the matrix material being doped with MR marker particles, and the peripheral section comprises an undoped, non-ferromagnetic matrix material.

Furthermore, according to the invention, a medical device with at least one control cord shown above is provided.

The medical device may comprise or be formed from a solid material body, such as a steerable guidewire. Here, at least one control cord is provided in a central lumen to control a tip or distal end of the guidewire.

The medical device according to the invention may comprise at least one tubular sheath wall delimiting a lumen, wherein a control cord as described above is arranged in the lumen, in particular a central lumen, and/or in at least one or more peripheral lumens formed in the sheath wall.

The medical device may be a steerable catheter, a steerable ablation catheter, a steerable sheath, a stent delivery system, a delivery system for occluders, a delivery system for coils, an atrial flow regulator delivery system, a bioptome, a TAVR, TMVR & LAA delivery system, a thrombectomy system, a steerable guidewire or the like.

In particular, the medical device may have two, three, four or more control cords.

By means of two control cords, a movement in two directions (two-dimensional) is possible. If at least three or four control cords are provided, movement in four directions, i.e. in space (three-dimensional), is possible.

The control cord may have the attachment portion at a distal end, by which the control cord is connected to the medical device at a distal end.

The connection of the control cord to the medical device can be designed as a material connection. The material connection can be made, for example, by welding or 3D printing or an additive manufacturing process.

A materially bonded connection is understood to comprise all connections in which the connecting partners are held together by atomic or molecular forces. At the same time, they are non-detachable connections, e.g. by means of welding, glueing, vulcanizing, which can only be separated by destroying the connecting means.

For this purpose, the fastening section may additionally and/or alternatively have a suitable connecting material or a suitable connecting material may have been applied to the fastening section.

The connection of the control cord with the medical device can be designed as a positive connection, which is formed by an interlocking of at least two connecting means. This means that the connecting partners cannot come loose even without or in the event of interrupted power transmission.

Herein, the fastening section of the control cord can be designed as a first form-fitting connecting means, such as rivets, screws, threaded connections, clips, latching elements, hooks, eyelets, lugs or rear cut-type connecting means, or the fastening section can be designed as a first separate form-fitting, possibly correspondingly designed, connecting means, such as rivets, screws, threaded connections, clips, latching elements, hooks, eyelets, lugs or rear cut-type connecting means.

A corresponding second positive connection means may be provided or formed at the distal end of the medical device.

The first and second connecting means are thus designed to form a positive connection.

In addition and/or as an alternative to the positive connection, the connection of the control cord to the medical device can be designed as a non-positive connection. In this case, a normal force acts on the surfaces to be connected. Their mutual displacement is prevented as long as the counter-force caused by the static friction is not exceeded.

Here, the fastening section of the control cord can be formed as a first non-positive connecting means or the fastening section can have a first separate non-positive connecting means.

A corresponding second non-positive connection means is provided or formed at the distal end of the medical device.

The first and second connecting means can be designed to transmit shear and/or tensile forces.

An MR-safe control cord can be manufactured, for example, by means of a strand drawing process. A pultrusion process is a continuous manufacturing process for the production of fiber-reinforced plastic profiles, whereby the fibers are impregnated with a chemically reactive polymer in the pultrusion process, which is cross-linked (synonyms: polymerized, cured) in the subsequent course of the process. However, it is also possible to produce corresponding fiber plastic-based control cords by means of extrusion, whereby the fibers are impregnated under pressure with heated, chemically non-reactive (already cross-linked) polymer. A suitable system for the production of a structured extrudate, comprising a special extrusion head, is described in WO 2017/037130.

The basic structure of a pultrusion plant is formed by a fiber rack, fiber guides, an impregnation device, a shaping tool and a curing tool, a drawing device and, if necessary, a cutting unit.

In open pultrusion processes, the fibers or fiber bundles are guided via fiber guides from a (possibly multi-level) spool tree into a starting matrix material bath, i.e. the reactive polymer/resin material, the impregnation device. The fibers or fiber bundles can pass through one or more shaping tools so that they are guided to the desired profile shape. Mats, fabrics, scrims or nonwovens can be integrated into the process at the fiber guides in order to adapt or optimise the mechanical properties compared to those of a purely unidirectional reinforcement as achieved by fibers or fiber bundles.

In the so-called closed process, the entire fibers or fiber bundles first come into contact with the starting matrix material in the shaping tool, but then with increased pressure for better impregnation. In the curing tool, the starting matrix material reacts to form the cross-linked matrix material (polymer/resin). The partially or predominantly cured pultrudate is drawn through a caterpillar haul-off, whereby the fibers or fiber bundles together with the starting matrix material are drawn out of the impregnation device into the shaping tool and the curing tool.

Basically, a distinction can be made between the three methods of resin impregnation: tub method, pull-through method and injection method.

The tub process is the most common process for producing pultruded profiles, especially with simple cross-sections. Impregnation takes place in an open starting matrix material bath through which the dry fibers or fiber bundles are drawn. The fibers or fiber bundles are deflected into and out of the initial matrix material bath by guide orifices.

The drawing-through process is used in particular for the production of profiles with geometrically complex cross-sections. The fibers or fiber bundles are guided through the initial matrix material bath without deflection, so that the impregnation device is passed through horizontally. At the inlet and outlet side of the bath with starting matrix material there are shaping tools that resemble the later profile shape. The starting matrix material that is stripped by the fiber guides is collected under the impregnation device with the help of a trough.

In the injection process, the fibers or fiber bundles are guided without deflection through the impregnation device, which has the shape of the profile to be produced and expands inside. In this cavity, the starting matrix material is injected from both sides transversely to the direction of the fibers. This process is used for the production of simple profiles with high production quantities. In a temperature-controlled tool with a length of 0.5 m to 2.5 m, the final shaping of the profile and the hot curing take place at temperatures between 100° C. and 200° C. The finished profile and thus the fibers or fiber bundles together with the starting matrix material are continuously conveyed by a subsequent drawing device, e.g. in the form of a caterpillar haul-off or pneumatic grippers, and pulled out of the tool at a constant speed.

The drawing speed of the process is adapted to the diameter of the profile, the complexity of the profile cross-section and the matrix material. A process speed of 0.1 m/min to 1.2 m/min is common.

Preferably, however, a pultrusion device for producing a pultrudate, in particular for producing an MR-safe control cord according to the invention, is provided according to the invention. This comprises:

at least one first spool system for feeding reinforcing material, in particular at least one reinforcing fiber, a first pultrusion head comprising a first housing, the housing having a radially circumferential first side wall, and whereas at a front end of the housing in the direction of production a first outlet nozzle and at the rear end opposite to the direction of production a first guide channel system are positioned, whereas the space in the housing between the guide channel system, the side wall and the outlet nozzle delimits a first impregnation space for impregnating the at least one reinforcing fiber with a starting matrix material, and the housing being arranged in the region of the impregnation space, the side wall and the outlet nozzle delimits a first impregnation space for impregnating the at least one reinforcing fiber with a starting matrix material, and whereas the housing in the region of the impregnation space is connectable to a first feeding system for the starting matrix material, and whereas within the guide channel system as least one guide channel extending in the direction of production is provided, in order to introduce at least one reinforcement fiber from the feeding system for at least one reinforcment fiber up to the impregnation space, and whereas the at least one guide channel is arranged in approximately straight alignment with the outlet nozzle, whereas the guide channel extends over the entire length of the guide channel system.

In the context of the present invention, the guide channel device can be designed as a quill, similar to the quills for extrusion devices known in the prior art (for applying extrudate radially circumferentially and uniformly to a body), for applying starting matrix material radially circumferentially and uniformly to a body.

According to the invention, the pultrusion head may also comprise only a housing, a guide channel system with at least one guide channel and an impregnation chamber for applying matrix material to the reinforcing fiber, and an outlet nozzle.

According to the invention, a target diameter of the arrangement of the fibers relative to each other is defined at the exit from the guide channel or is determined by the latter.

A starting matrix material may be a reactive polymer or resin material and comprise small non-crosslinked units or monomers. These monomers are not cured or polymerized or cross-linked in the starting matrix material.

An intermediate pultrudate can have a partially cross-linked or low grade cross-linked matrix material, whereby this pultrudate has a certain stiffness.

A final pultrudate can have a more highly cross-linked matrix material (polymer/resin), whereby this is not necessarily completely cross-linked in the pultrudate. Optionally, an additional heat treatment of the pultrudate for further cross-linking and curing of the matrix material can be added after pultrusion.

The advantages of the pultrusion device according to the invention will be shown later on the basis of a pultrusion process according to the invention and apply analogously to the pultrusion device.

With the pultrusion device, a predefined and relatively precise geometric arrangement of one or more reinforcing fibers in the control cord is possible.

In order to achieve a stable regular impregnation of one or more reinforcing fibers, a pultrusion head according to the invention is used to impregnate the reinforcing fibers with the starting matrix material at low pressure and to impregnate them substantially homogeneously.

The application of the starting matrix material by the pultrusion head avoids the deflection of the one or more reinforcing fibers and thus enables a better impregnation quality, since the one or more reinforcing fibers are guided exclusively linearly and these are not pressed flat at the deflection rollers and uncontrolled starting matrix material is stripped off. By applying pressure to the one or more reinforcing fibers with starting matrix material, the impregnation of the individual fibers is further improved.

Furthermore, a feeding device may be provided comprising at least a first spool tree for feeding at least one reinforcing fiber.

The guide channel is preferably a central guide channel.

The first outlet nozzle may have a nozzle disc with a nozzle opening for shaping an outer diameter of the impregnated reinforcing fiber.

Downstream of the pultrusion head, a first heating device is arranged for low-grade cross-linking of the starting matrix material, whereby an intermediate pultrudate with a low-grade cross-linked matrix material and a certain stiffness is obtained.

Examples of cross-linking reactions are radical polymerizations of monomers with two vinyl functions or polycondensation or polyaddition using monomers with two or more functionalities (e.g. in phenoplastics). The cross-linking of already existing polymers is also referred to as cross-linking and can either take place via functionalities already present in the polymer through clever choice of reaction conditions (self-cross-linkers), or can be accomplished through the addition of multifunctional, low-molecular substances, the cross-linking agents. Depending on the degree of cross-linking, the cross-linking of polymers first produces elastomers and, with increasing cross-linking, also duroplasts.

A second pultrusion head can be arranged after the heating device in the direction of production. This comprises

- at least one second spool tree for feeding reinforcing material, in particular at least one reinforcing fiber,
- a second housing, wherein the housing has a radially circumferential second side wall, wherein at a front end of the housing in the direction of production a nozzle disc is positioned and at the rear end opposite to the direction of production a guide channel system is positioned, wherein the space in the housing between the guide channel system, the side wall and the outlet nozzle delimits a second impregnation space for impregnating the reinforcing fiber with a starting matrix material, and wherein the housing can be connected in the region of the impregnation space to a feeding system for the starting matrix material, and wherein in the guide channel system at least one second central guide channel extending in the direction of production is providerd in order to introduce the intermediate pultrudate from the first heating device into the second impregnation chamber, and whereas the central guide channel is arranged approximately rectilinear alignment with the outlet nozzle, whereas the central guide channel extends over the entire length of the guide channel system, and wherein at least one peripheral guide channel is provided in order to introduce at least one second reinforcing fiber from a second system for feeding at least one reinforcing fiber into said second impregnation space, whereas said peripheral guide channel is positioned adjacent to said central guide channel, whereas the at least one peripheral guide channel extends along the entire length of said guide channel system.

The nozzle disc can be designed to fix or define an outer diameter of the final pultrudate, preferably a control cord.

Optionally, a second nozzle disc can be provided after the pultrusion head in order to finally fix or adjust the outer diameter of the final pultrudate, preferably of a control cord.

Downstream of the second pultrusion head, an arrangement member may be provided for arranging the intermediate pultrudate and the impregnated at least one second reinforcing fiber relative to each other.

In the direction of production, a second heating device is arranged downstream of the second pultrusion head for higher-grade cross-linking of the starting matrix material.

The first and/or the second pultrusion head may be connected to one or each pump for feeding the starting matrix material. In addition, each impregnation chamber can have a valve for discharging excess starting matrix material.

Furthermore, according to the invention, a pultrusion process is provided for producing a pultrudate, in particular a control cord. This comprises the following steps:

- introduction of a reinforcing material, in particular a reinforcing fiber, into a guide channel of a first pultrusion head,
- impregnating the reinforcing fiber in a first impregnation chamber of the first pultrusion head with a starting matrix material, preferably with a starting matrix material doped with MR marker particles,
- forming an outer diameter for the initial matrix material during exit from the first impregnation chamber by means of an exit nozzle,
- heating for low-grade cross-linking of the starting matrix material in a first heating device, obtaining an intermediate pultrudate,
- introduction of the intermediate pultrudate into a central guide channel of a second pultrusion head,
- introduction of at least one further reinforcing fiber into at least one peripheral guide channel of the second pultrusion head,
- impregnating the at least one further reinforcing fiber in a second impregnation chamber of the second pultrusion head with a starting matrix material,
- positioning the intermediate pultrudate and the impregnated reinforcing fiber relative to each other during exit from the second impregnation space by means of a nozzle disc, and heating and higher degree cross-linking of the matrix material in a second heating device.

The central reinforcing fiber can fray apart and/or migrate from the centric position in the pultrusion processes in the prior art, since stabilization of the geometric arrangement is no longer possible after exiting the impregnation bath or from entering the heating element. This results in an uncontrolled spatial and/or linearly indeterminate non-centered arrangement. In order to impregnate the reinforcement fibers with starting matrix material, they must also be deflected into the starting matrix material bath via rollers. This creates unilateral pressure on the reinforcing fibers, which impairs the homogeneity of the impregnation and its geometric arrangement. The multiple deflection of the reinforcing fiber can also cause twisting and tension in the pultrudate.

Alternatively, a pultrudate with a central section and a peripheral section can be produced in two separate, successive pultrusions according to the state of the art. For this purpose, the central section is first produced as a first pultrudate and the matrix material is cross-linked to a higher degree so that it achieves a customary stiffness. This first pultrudate is then introduced into a second, separate pultrusion after curing as a central element which is surrounded by further reinforcing fibers. The disadvantage is that the curing of the first pultrudate creates a material boundary at the surface of the first pultrudate to the matrix material from the second pultrusion, resulting in a weak point in the material. This disadvantage is avoided by the consecutive pultrusion process according to the invention in a single pultrusion, since the intermediate pultrudate is only cross-linked to a low degree. Furthermore, a single consecutive pultrusion process is technically and economically advantageous because it can be carried out at lower cost and in less time.

With the pultrusion process according to the invention, a substantially improved linearity and a substantially improved centeredness of the central doped section in the pultrudate in the longitudinal direction can be ensured than with a pultrusion process according to the prior art, in which the central section formed by the first reinforcing fiber can deviate significantly from the zero line.

The pultrudate may comprise a plurality of reinforcing fibers, preferably with one reinforcing fiber centrally located and surrounded by a plurality of reinforcing fibers.

The intermediate pultrudate for the central section is first cross-linked to a low degree in order to prevent fraying of the reinforcing fibers and to achieve sufficient stiffness through the low degree cross-linking to enable a stable centric arrangement in the final pultrudate. In general, the better the geometric arrangement of the individual reinforcing fibers in a pultrudate formed from several reinforcing fibers, the better the mechanical properties of the pultrudate.

In order to achieve an improved stable geometrical arrangement of all reinforcing fibers in the pultrudate and a stable regular impregnation of all reinforcing fibers, a first and a second pultrusion head are provided to impregnate the reinforcing fibers with starting matrix material at low pressure without deflection in an impregnation device and to impregnate them homogeneously. In this way, the individual reinforcing fibers are arranged in the pultrudate without the risk of displacement or flattening of reinforcing fibers. The application of the starting matrix material by a pultrusion head avoids the deflection of the reinforcing fibers and also enables a better impregnation quality, because the reinforcing fibers are exclusively guided linearly and impregnated with pressure.

The central reinforcing fiber is impregnated with starting matrix material, which may contain marker particles, in the first pultrusion head, which comprises a linear guide channel, and is passed through a first heating device in a second step, in which the low-degree cross-linking of the starting matrix material takes place. This achieves a defined stiffness of the intermediate pultrudate. The pultrusion head contains a feed for starting matrix material, which is fed e.g. via a pump, and a discharge for excess starting matrix material, whereby the excess starting matrix material can be returned to the feed.

At the distal end of the first pultrusion head 1, a nozzle disc may be arranged to define the outer diameter (round) or the cross-sectional profile (shapes other than round) and to strip off excess starting matrix material.

In the third step, the intermediate pultrudate can be introduced into a central guide channel of a second pultrusion head. Peripheral reinforcing fibers can be introduced into peripheral guide channels of the second pultrusion head and impregnated with starting matrix material.

An arrangement element can be provided at the outlet of the second production head distal in the direction of production, which can be designed integrally or separately. This arrangement element defines the central arrangement of the intermediate pultrudate and the peripheral reinforcing fibers impregnated with starting matrix material in the pultrudate and strips off excess starting matrix material.

The arrangement element contains openings, e.g. holes, which correspond to the desired geometrical arrangement of the reinforcing fibers in the pultrudate. In the fourth step, this reinforcing fiber arrangement is introduced into a second heating element and the matrix material is cross-linked to a higher degree as it passes through it.

According to the invention, pultruded products with changing matrix materials can be produced with the pultrusion device described above. Only one pultrusion head is required to produce a pultrudate without a central and a peripheral section. In a pultrusion head according to the invention, the fed starting matrix material can be changed quickly and in a controlled manner, so that alternating sections (main sections, deflection section) can be produced with the first and the second matrix material over defined lengths. For this purpose, one or more sufficiently small feed devices for the starting material and a correspondingly small impregnation chamber are provided, which are designed depending on the diameter of the pultrudate to be produced and allow the starting matrix material to be changed quickly.

In the following, exemplary embodiments of a control cord according to the invention are shown.

According to a first embodiment example, the control cord has a diameter of, for example, approx. 0.25 to 0.3 mm. Only aramid fiber bundles are provided as fiber bundles. These have a fineness of at least about 6 tex or at least about 22 tex and preferably of at least about 11 tex. The matrix material is doped with MR marker particles.

In a second embodiment, the control cord has a diameter of, for example, 0.3 to 1 mm or of approximately 0.3 mm or 0.2 mm or 0.3 mm or 0.4 mm to 0.5 mm to 0.6 mm or 0.7 mm or 0.8 mm 0.9 mm or 1 mm. Only aramid fiber bundles are provided as fiber bundles. These have a fineness of at least about 66 tex or at least about 33 tex, or at least about 22 tex and preferably at least about 11 tex. The matrix material is doped with MR marker particles.

In a third embodiment example, one or more aramid fiber bundles of the control cord are arranged in the central section. The fiber bundles arranged in the peripheral section are partly aramid, for example about 80% by volume 65% by volume, 50% by volume 35% by volume, and partly glass fiber bundles, for example about 20% by volume 35% by volume, 50% by volume 65% by volume. The diameter of the central section is about 0.15 mm or 0.2 mm or 0.25 mm or 0.3 mm to 0.35 mm or 0.4 mm or 0.45 mm or 0.5 mm. The greater the amount of fineness [Tex], the greater the diameter of the central section. The control cord has a diameter of, for example, 0.3 mm or 0.4 mm or 0.5 mm or 0.6 mm to 0.7 mm or 0.8 mm or 0.9 mm or 1 mm. The matrix material is doped with MR marker particles.

In a fourth embodiment, one or more central aramid fiber bundles of the control cord are arranged in the central section and the matrix material of the central section is doped with MR marker particles. The aramid fiber bundles have a fineness of at least about 6 Tex or at least about 22 Tex, and preferably at least about 11 Tex. In contrast, the aramid fiber bundles arranged in the peripheral section are embedded in non-doped matrix material. The diameter of the central section is about 0.07 mm to 0.15 mm. The greater the amount of fineness [Tex], the greater the diameter of the central section. The control cord has a diameter of about 0.25 to 0.3 mm, for example.

In a fifth embodiment, one or more aramid fiber bundles of the control cord are arranged in the central section and the matrix material of the central section is doped with MR marker particles. The fiber bundles arranged in the peripheral section are partly aramid, e.g. about 80% by volume 65% by volume, 50% by volume 35% by volume, and partly glass fiber bundles, e.g. about 20% by volume 35% by volume, 50% by volume 65% by volume, which are embedded in non-doped matrix material. The diameter of the central section is about 0.07 mm to 0.15 mm or about 0.1 mm to 0.2 mm or about 0.15 mm to 0.3 mm or about 0.15 mm to 0.4 mm or about 0.15 mm to 0.50 mm or about 0.15 mm to 0.50 mm, respectively. The greater the amount of fineness [Tex] of the aramid fiber bundles, the greater the diameter of the central section. The control cord has a diameter of, for example, 0.25 to 1.00 mm or 0.3 mm or 0.4 mm or 0.5 mm or 0.6 mm to 0.7 mm or 0.8 mm or 0.9 mm or 1 mm. The matrix material is doped with MR marker particles.

The above-mentioned embodiments of the present invention can be combined with each other in any way, if technically possible.

While this invention has been particularly shown and described with references to preferred embodiments thereof, it will be understood by those skilled in the art that various changes in form and details may be made therein without departing from the scope of the invention encompassed by the appended claims.

What is claimed is:

1. A magnetic resonance imaging (MR) safe control cord for controlling a medical device, wherein the control cord can be arranged in a medical device, wherein the control cord is formed from a non-ferromagnetic matrix material in which a reinforcing material is embedded, and wherein the control cord is structurally designed in such a way that the medical device can be controlled by displacing the control cord in and against an axial direction of a medical device, or that a functional element of a medical device which can be coupled to the control cord can be controlled, wherein the control cord has at least one deflection section, the deflection section being formed with matrix materials having a lower stiffness and a higher flexibility than in the remaining region of the control cord.

2. The MR-safe control cord according to claim 1, wherein the matrix material is doped with magnetic resonance imaging artifact-generating marker particles such that the medical device is visible in magnetic resonance imaging by these marker particles.

3. The MR-safe control cord according to claim 2, wherein the magnetic resonance imaging artifact-generating marker particles are arranged over substantially the entire length of the control cord such that the medical device is visible in magnetic resonance imaging over substantially its entire length.

4. The MR-safe control cord according to claim 2, wherein the control cord comprises one or more X-ray markers.

5. The MR-safe control cord according to claim 1, wherein the deflection section is configured to be arranged at a deflection point of the medical device at which the control cord is deflected.

6. The MR-safe control cord according to claim 1, wherein the control cord is a one-piece solid body and is not a tubular or hose-shaped hollow body.

7. The MR-safe control cord according to claim 1, wherein a transition between the matrix material in the deflection section and the matrix material in the remaining region comprises a material gradient.

8. The MR-safe control cord according to claim 1, wherein the control cord is structurally designed in such a way that it can be arranged in one or more lumens of a tubular medical device, including a central lumen, a lumen in a sheath wall, or both, and wherein the control cord has a diameter of 0.02 mm to 1 mm, i.e. of 1 mm, or smaller than 0.9 mm, or smaller than 0.8 mm, or smaller than 0.7 mm, or smaller than 0.6 mm, or smaller than 0.5 mm, or smaller than 0.4 mm, or smaller than 0.3 mm, or smaller than 0.2 mm, or smaller than 0.1 mm, or smaller than 0.05 mm.

9. The MR-safe control cord according to claim 1, wherein the control cord has one or more of the following features:

the matrix material is a duroplastic or a thermoplastic polymer;

the reinforcing material comprises one or more reinforcing fibers which are formed as fibers, filaments, fiber bundles, filament bundles which extend over approximately the entire length of the control cord;

the control cord has an elongation at break of 4% to 1%, which is a maximum of 4% or 3.5% or 3% or 2.5% or 2% or 1.5% or 1%;

and the control cord has an ultimate tensile strength of 3.5 to 6.0 GPa, which is at least 3.5 GPa or 4 GPa or 4.5 GPa or 5 GPa or 5.5 GPa and at most 6 GPa.

10. The MR-safe control cord according to claim 1, wherein the control cord comprises a central section and a peripheral section extending in the axial direction of the control cord, the central section being centrally located with respect to a cross-section of the control cord and being radially surrounded by the peripheral section, and whereas both the central section and the peripheral section extend substantially over the entire length of the control cord, and the central section comprises at least one non-metallic reinforcing material embedded in a non-ferromagnetic matrix material, the matrix material being doped with MR marker particles, and the peripheral section comprises an undoped, non-ferromagnetic matrix material.

11. A medical device having at least one MR safe control cord according to claim 1.

12. The medical device according to claim 11, wherein the medical device has a tubular jacket wall, and wherein the control cord is arranged in a central lumen delimited by the tubular jacket wall or in a peripheral lumen formed in the tubular jacket wall.

13. The medical device according to claim 12, wherein the control cord has at least one fastening section at a distal end, via which the control cord is connected to a distal end of the tubular jacket wall.

* * * * *